(12) United States Patent
Seitzinger et al.

(10) Patent No.: US 6,234,635 B1
(45) Date of Patent: May 22, 2001

(54) METHOD FOR PREVENTING LAPAROSCOPE FOGGING

(76) Inventors: Michael R. Seitzinger, 1960 Belle Mapps Ct., Greenlake, WI (US) 54941; David Platts, 1931-B 42nd St., Los Alamos, NM (US) 87544

( * ) Notice: Subject to any disclaimer, the term of this patent is extended or adjusted under 35 U.S.C. 154(b) by 0 days.

(21) Appl. No.: 09/126,266

(22) Filed: Jul. 30, 1998

(51) Int. Cl.[7] .............................. G02B 11/04; A61B 1/06
(52) U.S. Cl. .......................................... 359/512; 600/169
(58) Field of Search ............................ 359/512; 600/169

(56) References Cited

U.S. PATENT DOCUMENTS 1,791,254 * 2/1931 Von Brockdorff ................... 359/512
5,647,840 * 7/1997 D'Amelio et al. ................... 600/169

* cited by examiner

*Primary Examiner*—Cassandre Spyrou
*Assistant Examiner*—Jared Treas
(74) *Attorney, Agent, or Firm*—Samuel M. Freund

(57) ABSTRACT

The present invention includes maintaining the region of the proximal lens of a laparoscope at greater than ambient temperature in order to prevent fogging during use. Heating is accomplished using commercially available chemical heat packs generally used for heating boots or gloves. The invention differs from other anti-fogging devices, which either immerse the distal lens region of the laparoscope in a warm fluid or treat this lens with anti-fogging solutions, in that above-ambient temperature is continuously maintained throughout the laparoscope, since it is known that a cool laparoscope fogs when placed in the vicinity of warm, wet tissue.

3 Claims, 1 Drawing Sheet

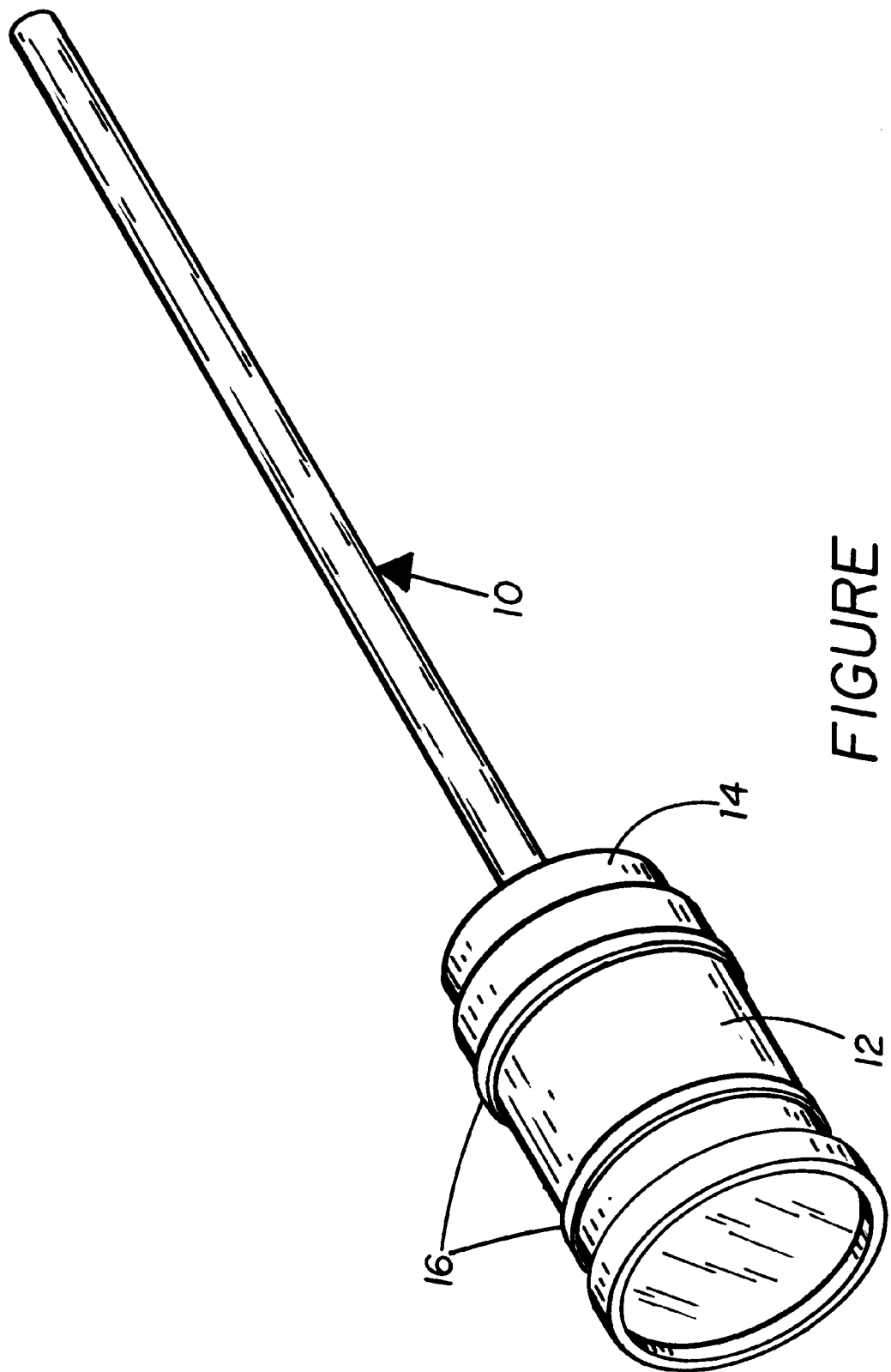
FIGURE

METHOD FOR PREVENTING LAPAROSCOPE FOGGING

FIELD OF THE INVENTION

The present invention relates generally to a method for defogging laparoscopes during surgery and, more particularly, to the use of a heat source in the region of the proximal lens to maintain a chosen temperature difference between the laparoscope and ambient temperature.

BACKGROUND OF THE INVENTION

Laparoscope fogging remains a nagging problem occurring in almost all procedures, and appears to be the result of the presence of a cold lens or other optical surface in a warm, moist environment. Techniques addressing this difficulty abound, but no one answer has emerged as the ultimate solution. Antifogging solutions that are wiped on the lens are common, but are criticized for possibly scratching the optic and for only briefly addressing the problem. Heating the laparoscope to more closely match the temperature of the body is also common, but it is thought that such procedures bake debris into the laparoscope. A variation of this latter method is achieved by rinsing the laparoscope after a cold sterilization process with warm sterile water and taking the warmed laparoscope quickly to the field. For treating a fogged laparoscope in the field, a commercially available product known as the Laparoscopic Scope Warmer manufactured by Applied Medical Resources, is a double-walled thermos filled with warm water having padding inside to cushion the lens. A disposable seal is placed over the top of the device to provide insulation while permitting insertion of the laparoscope. The warm water heats the laparoscope sufficiently to clear the fogging and has the additional feature of rising off debris. See, e.g., "Tactics Cope With Scope Fogging," in Laparoscopic Surgery Update, Sample Issue (1995), pages 5 and 6.

Accordingly, it is an object of the present invention to reduce fogging of laparoscopic lenses without having to apply antifogging solutions to the distal end thereof.

Another object of the present invention is to reduce fogging of laparoscopic lenses without having to remove the laparoscope from the patient for defogging during surgery.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for preventing laparoscope fogging, of the invention includes the step of maintaining the temperature of the laparoscope in the region of the proximal lens at above ambient temperature.

Preferably, the region of the proximal lens of the laparoscope is maintained at between 35° C. and 50° C.

It is also preferred that the step of maintaining the temperature of the laparoscope in the region of the proximal lens at above ambient temperature is achieved by wrapping a chemical or phase-change salt heat pack around the region of the proximal lens of the laparoscope.

Preferably also, the chemical heat pack is sterilized using gamma radiation.

Benefits and advantages of the present invention include the maintenance of an unfogged condition of the laparoscopic lenses during surgical procedures without having to remove the laparoscope from the operating field, which can significantly slow progress of the procedures, and without the need for electrical components or harsh chemical defoggers.

BRIEF DESCRIPTION OF THE DRAWING

The accompanying drawing, which is incorporated in and forms a part of the specification, illustrates one embodiment of the present invention and, together with the description, serves to explain the principles of the invention.

The FIGURE is a schematic presentation of a side view of a typical laparoscope showing the chemical heat pack wrapped around the region of the proximal lens of the laparoscope for heating both the proximal and distal lens regions of the laparoscope.

DETAILED DESCRIPTION

Briefly, the present invention includes maintaining the region of the proximal lens of a laparoscope at greater than ambient temperature in order to avoid fogging during use. Heating may be accomplished by using commercially available chemical heat packs generally used for heating boots or gloves, phase-change salt heat packs, or electrical heating apparatus. The invention differs from other anti-fogging devices, which either immerse the distal lens region of the laparoscope in a warm fluid or treat this lens with antifogging solutions, in that above-ambient temperature is continuously maintained throughout the laparoscope, since it is known that a cool laparoscope fogs when placed in the vicinity of warm, wet tissue. The proximal lens region of the laparoscope is the region of the eyepiece or a camera/lens junction of the laparoscope, depending on the type of laparoscope.

Reference will now be made in detail to the present preferred embodiments of the invention, examples of which are illustrated in the accompanying drawing. Turning now to the FIGURE, a schematic representation of a side view of a commercially available laparoscope, 10, is shown. Heating device, 12, is attached in the region of the proximal lens end of the laparoscope, 14, such that the heating device does not interfere with the operation of the proximal lens during use of the laparoscope. Preferably, the heating device includes commercially available chemical heat packs that commonly include iron powder, sodium chloride, vermiculite, water, and activated charcoal. The heat packs are pre-sterilized and sealed in sterile packaging. Gamma radiation has been found to be effective for sterilization, although ethylene oxide may be used. Prior to use, the heat pack is removed from the packaging, shaken to mix the contents thereof and activate the chemical reaction. The activated pack is then wrapped around the proximal end of the laparoscope and fastened thereto using steri strips, 16. In bench tests, where heat packs were activated and wrapped around stainless steel thermometers, gamma radiation-sterilized packs were found to attain temperatures between 40° C. and 50° C. in approximately 30 min., and remain in this temperature range for about 6 h, after which the temperature was observed to decrease slowly in time. In actual surgical testing, laparoscopes heated according to the teachings of the present invention remained fog-free for several hours.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preventing laparoscope fogging, which comprises the step of maintaining the temperature of the laparoscope in the region of the proximal lens at between 35° C. and 50° C. by wrapping a chemical heat pack around the region of the proximal lens of said laparoscope.

2. The method for preventing laparoscope fogging as described in claim 1, wherein the chemical heat pack comprises iron powder, sodium chloride, vermiculite, water, and activated charcoal.

3. The method for preventing laparoscope fogging as described in claim 1, wherein the chemical heat pack is sterilized using gamma radiation.

* * * * *

UNITED STATES PATENT AND TRADEMARK OFFICE
CERTIFICATE OF CORRECTION

PATENT NO. : 6,234,635 B1
DATED : July 25, 2001
INVENTOR(S) : Seitzinger et al.

It is certified that error appears in the above-identified patent and that said Letters Patent is hereby corrected as shown below:

<u>Column 3, line 12 - Column 4, line 3,</u>
Claim 1, should read as follows:

-- A method for preventing laparoscope fogging, which comprises the step of maintaining the temperature of the laparoscope in a region of a proximal lens between 35 degrees Centigrade and 50 degrees Centigrade by wrapping a chemical heat pack around the lens proximal to a viewer of said laparoscope. --

Signed and Sealed this

Twelfth Day of October, 2004

JON W. DUDAS
*Director of the United States Patent and Trademark Office*